United States Patent
Abir Cavalero et al.

(10) Patent No.: US 12,387,846 B2
(45) Date of Patent: *Aug. 12, 2025

(54) SYSTEMS, DEVICES, AND METHODS UTILIZING BIO-POTENTIAL DATA OBTAINED BY A PLURALITY OF BIO-POTENTIAL SENSORS FOR PRENATAL TRACKING

(71) Applicant: NUVO INT'L GROUP INC., Aventura, FL (US)

(72) Inventors: Gil Abir Cavalero, Tel Aviv (IL); Barak Laish, Tel Aviv (IL); Amit Reches, Tel Aviv (IL)

(73) Assignee: NUVO INT'L GROUP INC., Aventura, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/621,219

(22) Filed: Mar. 29, 2024

(65) Prior Publication Data
US 2024/0355473 A1 Oct. 24, 2024

Related U.S. Application Data

(63) Continuation of application No. 18/161,789, filed on Jan. 30, 2023, now Pat. No. 11,972,868.
(Continued)

(51) Int. Cl.
*G16H 50/20* (2018.01)
*G16H 50/70* (2018.01)

(52) U.S. Cl.
CPC ............. *G16H 50/20* (2018.01); *G16H 50/70* (2018.01)

(58) Field of Classification Search
CPC ............................ G16H 50/20; G16H 50/70
(Continued)

(56) References Cited

U.S. PATENT DOCUMENTS

| | | | | |
|---|---|---|---|---|
| 8,396,229 B2 * | 3/2013 | Oz | ......................... | A41F 9/002 |
| | | | | 181/126 |
| 2005/0267377 A1 * | 12/2005 | Marossero | ......... | A61B 5/02411 |
| | | | | 128/920 |

(Continued)

OTHER PUBLICATIONS

National Guideline Alliance (UK), Addendum to intrapartum care: care for healthy women and babies. London: National Institute for Health and Care Excellence (NICE); Feb. 2017 (Clinical Guideline, No. 190.1.) Appendix J, Fetal heart rate classifications. https://www.ncbi.nlm.nih.gov/books/NBK550641/ (Year: 2017).*
(Continued)

*Primary Examiner* — Joy Chng
(74) *Attorney, Agent, or Firm* — Greenberg Traurig, LLP

(57) ABSTRACT

A method includes receiving an input data set for an expectant mother during a time window, the input data set including fetal heart rate data; completing the input data set with a missing data sample to produce a completed data set; removing a segment from the completed data set based a criterion to produce a corrected data set; calculating a baseline fetal heart rate based on the corrected data set; detecting an event occurring during the time window based on the corrected data set and/or the baseline fetal heart rate; classifying the event as either an acceleration, a deceleration, or a baseline change based on the corrected data set and/or the baseline fetal heart rate; and generating an output indicative of the event to enable an action with respect to the expectant mother.

20 Claims, 10 Drawing Sheets

Related U.S. Application Data

(60) Provisional application No. 63/304,120, filed on Jan. 28, 2022.

(58) Field of Classification Search
USPC .......................................................... 705/2–3
See application file for complete search history.

(56) References Cited

U.S. PATENT DOCUMENTS

| | | | |
|---|---|---|---|
| 2011/0098586 A1* | 4/2011 | Kabakov | A61B 5/7221 600/511 |
| 2012/0232398 A1* | 9/2012 | Roham | A61B 8/565 600/528 |
| 2014/0378855 A1* | 12/2014 | Dash | A61B 5/02411 600/511 |
| 2016/0270670 A1* | 9/2016 | Oz | A61B 5/352 |
| 2020/0113470 A1* | 4/2020 | Friedman | A61B 5/686 |
| 2020/0163644 A1* | 5/2020 | Groberman | A61B 8/488 |
| 2020/0196958 A1* | 6/2020 | Penders | A61B 5/0002 |

OTHER PUBLICATIONS

International Search Report and Written Opinion to corresponding International Application No. PCT/IB2023/000034 mailed Jul. 25, 2023 (11 pages).

\* cited by examiner

| | Baseline | Variability | Deceleration | Acceleration |
|---|---|---|---|---|
| Reassuring | 110-160 b.p.m. | ≥ 5 b.p.m. | Non | Present |
| Non-reassuring | 100-109 b.p.m. 161-180 b.p.m. | ≤ 5 b.p.m. for more than 40 minutes and less than 90 minutes | Early deceleration Variable deceleration Single prolong deceleration up to 3 minutes | The absences of acceleration with an otherwise normal CTG is of uncertain significant |
| Abnormal | <100 b.p.m. > 180 b.p.m. Sinusoidal pattern for more than 10 minutes | < 5 b.p.m. for more than 90 minutes | Late deceleration A typical variable deceleration Single prolong deceleration greater than 3 minutes | |

Figure 8

SYSTEMS, DEVICES, AND METHODS UTILIZING BIO-POTENTIAL DATA OBTAINED BY A PLURALITY OF BIO-POTENTIAL SENSORS FOR PRENATAL TRACKING

CROSS-REFERENCE TO RELATED APPLICATION

This application is a continuation of U.S. patent application Ser. No. 18/161,789, filed Jan. 30, 2023, entitled "SYSTEMS, DEVICES, AND METHODS UTILIZING BIO-POTENTIAL DATA OBTAINED BY A PLURALITY OF BIO-POTENTIAL SENSORS FOR PRENATAL TRACKING," which claims the benefit of commonly-owned, U.S. Provisional Patent Application No. 63/304,120, filed on Jan. 28, 2022 and entitled "SYSTEM, DEVICE, AND METHOD FOR PRENATAL CLINICAL DECISION SUPPORT," the contents of which are incorporated herein by reference in their entirety.

FIELD OF THE INVENTION

The present disclosure is related to systems and methods for providing clinical decision support to clinicians who are providing care to expectant mothers. More particularly, the present disclosure is related to systems and methods for providing clinical decision support based on the results of remote non-stress testing performed through the use of sensor-laden garments (e.g., garments such as belts having sensors such as bio-potential sensors and acoustic sensors).

BACKGROUND OF THE INVENTION

A non-stress test involves review of 20-40 minutes of fetal heart rate, maternal heart rate and uterine activity data. This data is manually reviewed by physicians or experienced nurses in order to decide if the test is concerning or reassuring. The clinicians viewing the data manually scan the data looking for relevant clinical phenomena, which are usually changes in the fetal heart rate. For example, these phenomena can include fetal heart rate accelerations, deceleration, or certain levels of fetal heart rate variability. The clinical relevance of some of these phenomena may change based on their temporal relation to the appearance of contractions in the uterine activity. Once these clinical phenomena are found, they are marked, and a set of rules defined by the American College of Obstetrics and Gynecology (ACOG) are followed in order to reach a clinical decision on whether the NST is reactive or non-reactive. Based on this decision, the next step in the clinical workflow is devised.

SUMMARY OF THE DISCLOSURE

In some embodiments, a method includes receiving, by a computing device, an input data set for an expectant mother during a time window, wherein the input data set includes at least fetal heart rate data, wherein the fetal heart rate data is calculated based at least on raw bio-potential data obtained by a plurality of bio-potential sensors in a garment worn by the expectant mother; completing, by the computing device, the input data set with at least one missing data sample to provide a completed data set; removing, by the computing device, at least one segment from the completed data set based on at least one criterion to provide a corrected data set; calculating, by the computing device, a baseline fetal heart rate based at least on the corrected data set; detecting, by the computing device, at least one event occurring during the time window based at least on at least one of the corrected data set or the baseline fetal heart rate; classifying, by the computing device, the at least one event as either an acceleration, a deceleration, or a baseline change based at least on at least one of the corrected data set or the baseline fetal heart rate; and generating, by the computing device, an output indicative of at least the at least one event, wherein the output is configured to enable at least one action being taken with respect to the expectant mother.

In some embodiments, the at least one criterion for the step of removing the at least one segment from the completed data set includes removing the at least one segment based on the at least one segment including a periodic change in the fetal heart rate. In some embodiments, the periodic change in the fetal heart rate includes at least one of (a) the fetal heart rate varying by more than 25 beats per minute in consecutive samples or (b) applying a threshold based on median and standard deviation.

In some embodiments, a method also includes determining, by the computing device, whether the input data set is valid or is not valid; and if the input data set is determined to be not valid, receiving a further input data set prior to the step of performing the completing, by the computing device, the input data set, wherein the step of completing, by the computing device, the input data set is performed on the further input data set. In some embodiments, the step of determining whether the input data set is valid or is not valid is performed by a process including: identifying, by the computing device, plurality of stable segments of the corrected data set, wherein each stable segment includes a sequence of a predetermined quantity of consecutive samples having a fetal heart rate variability that is less than a predetermined threshold variability; determining, by the computing device, a total duration of the plurality of stable segments; and; determining, by the computing device, whether the input data set is valid or is not valid based at least on a comparison of the total duration of the plurality of stable segments to a predetermined threshold duration.

In some embodiments, the step of determining, by the computing device, the baseline fetal heart rate is performed by a process including: calculating, by the computing device, a virtual baseline fetal heart rate; calculating, by the computing device, a virtual high fetal heart rate limit; calculating, by the computing device, a virtual low fetal heart rate limit; removing, by the computing device, outlier data points from the corrected data set, wherein outlier data points are data points having a fetal heart rate higher than the virtual high fetal heart rate limit or having a fetal heart rate lower than the virtual low fetal heart rate limit; and calculating, by the computing device, the baseline fetal heart rate based at least on applying rounding to the corrected data set following removing the outlier data points. In some embodiments, the virtual baseline fetal heart rate is a mean average of fetal heart rates in the corrected data set. In some embodiments, the steps of calculating the virtual high fetal heart rate limit and calculating the virtual low fetal heart rate limit are performed by a process including: calculating, by the computing device, a standard deviation for the virtual baseline fetal heart rate; calculating, by the computing device, the virtual high fetal heart rate limit as the virtual baseline fetal heart rate plus two times the standard deviation; and calculating, by the computing device, the virtual low fetal heart rate limit as the virtual baseline fetal heart rate minus two times the standard deviation.

In some embodiments, at least one of the at least one event is classified as an acceleration, and the at least one of the at least one event is classified as an acceleration based on a process including: identifying, by the computing device, a first intersection between a trace of the corrected data set and the baseline fetal heart rate; identifying, by the computing device, a second intersection between the trace of the corrected data set and the baseline fetal heart rate; identifying, by the computing device, a maximum fetal heart rate during a time interval between the first intersection and the second intersection; and identifying, by the computing device, the time interval as including the acceleration based at least on a duration of the time interval and the maximum fetal heart rate during the time interval. In some embodiments, the step of identifying the time interval as including the acceleration is further based on a gestational week of the expectant mother. In some embodiments, a method also includes determining, by the computing device, fetal heart rate baseline variability. In some embodiments, the step of determining, by the computing device, the fetal heart rate baseline variability is performed by a process including: determining, by the computing device, a highest fetal heart rate during a variability time interval following the second intersection, wherein the variability time interval extends from the second intersection until a sooner of (1) a predetermined duration following the second intersection or (2) onset of a subsequent acceleration or deceleration; determining, by the computing device, a lowest fetal heart rate during the variability time interval; and subtracting, by the computing device, the lowest fetal heart rate during the variability time interval from the highest fetal heart rate during the variability time interval to provide the fetal heart rate baseline variability.

In some embodiments, the at least one event includes a deceleration, and the at least one event is classified as a deceleration based on a process including: identifying, by the computing device, a first intersection between a trace of the corrected data set and the baseline fetal heart rate; identifying, by the computing device, a second intersection between the trace of the corrected data set and the baseline fetal heart rate; identifying, by the computing device, a minimum fetal heart rate during a time interval between the first intersection and the second intersection; and identifying, by the computing device, the time interval as including the deceleration based at least on a difference between the baseline fetal heart rate and the minimum fetal heart rate during the time interval. In some embodiments, a method also includes classifying, by the computing device, the deceleration as one of an early deceleration, a late deceleration, a variable deceleration, or a prolonged deceleration. In some embodiments, the input data set also includes a uterine contraction signal, and the deceleration is classified as the one of the early deceleration, the late deceleration, the variable deceleration, or the prolonged deceleration based on a process including: determining, by the computing device, a delay, wherein the delay is an amount of elapsed time between the first intersection and a time of the minimum fetal heart rate during the time interval; determining, by the computing device, a time of a peak of a uterine contraction during the time interval; determining, by the computing device, a time difference between the time of the minimum fetal heart rate during the time interval and the time of the peak of the uterine contraction signal during the time interval; and classifying, by the computing device, the deceleration as the one of the early deceleration, the late deceleration, the variable deceleration, or the prolonged deceleration based at least on the delay, the time difference, and a duration of the uterine contraction.

In some embodiments, two iterations of the steps of (1) removing, by the computing device, at least one segment from the completed data set based on at least one criterion to provide a corrected data set, (2) calculating, by the computing device, a baseline fetal heart rate based at least on the corrected data set, and (3) detecting, by the computing device, at least one event occurring during the time window based at least on at least one of the corrected data set or the baseline fetal heart rate, are performed for the time window.

In some embodiments, a method also includes repeating, for a subsequent time window, the steps of: receiving, by the computing device, an input data set for the expectant mother; completing, by the computing device, the input data set with at least one missing data sample to provide a completed data set; removing, by the computing device, at least one segment from the completed data set based on at least one criterion to provide a corrected data set; calculating, by the computing device, a baseline fetal heart rate based at least on the corrected data set; detecting, by the computing device, at least one event occurring during the time window based at least on at least one of the corrected data set or the baseline fetal heart rate; and classifying, by the computing device, the at least one event as either an acceleration, a deceleration, or a baseline change based at least on at least one of the corrected data set or the baseline fetal heart rate. In some embodiments, the subsequent time window does not overlap the time window. In some embodiments, the subsequent time window overlaps the time window by an overlap duration. In some embodiments, the overlap duration is between 5% of a duration of the time window and 95% of the duration of the time window.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

FIG. 8 shows an flowchart of exemplary criteria for classifying monitoring sessions based on FHR.

DETAILED DESCRIPTION OF THE DRAWINGS

Figure 1:
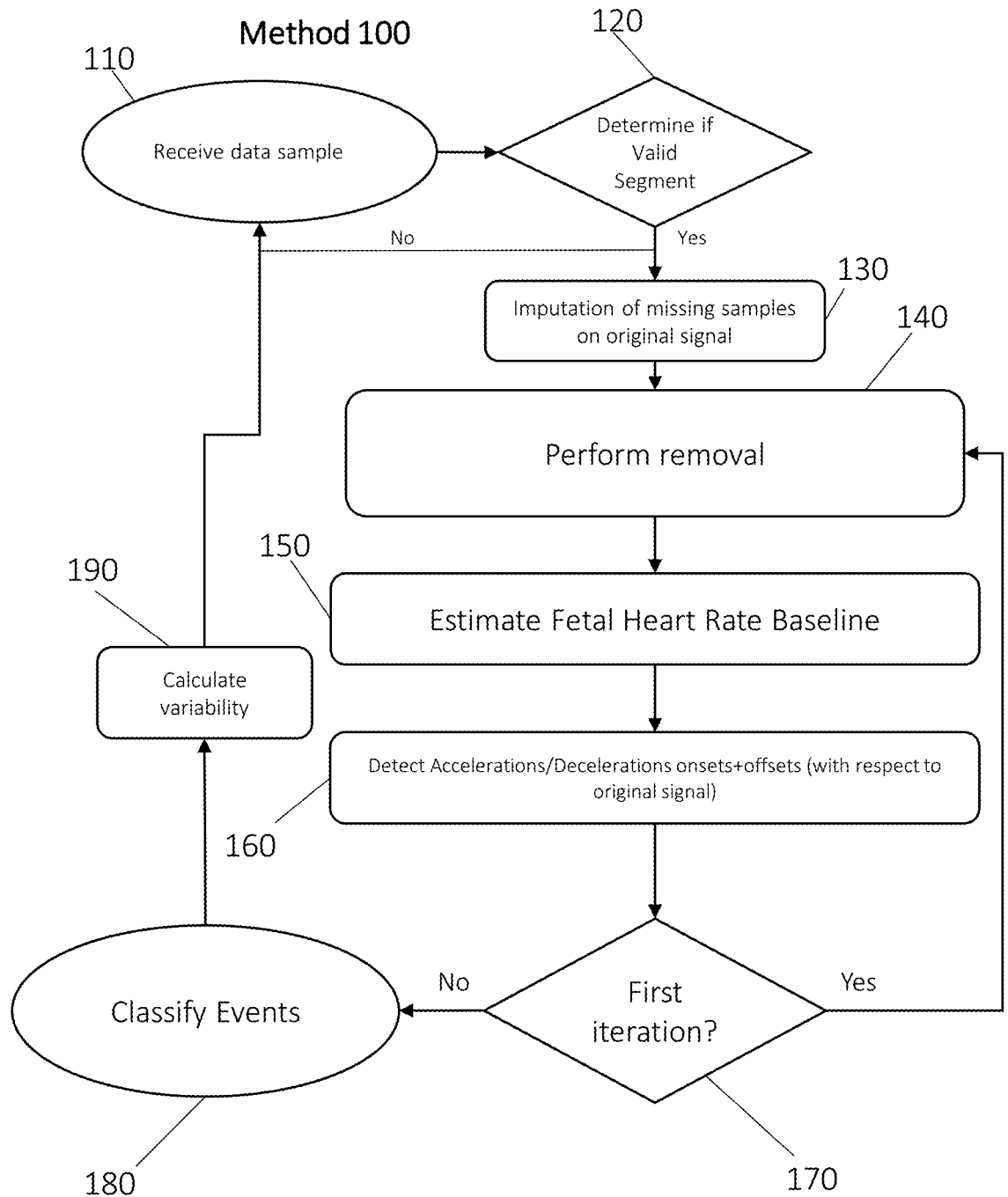
FIG. 1 shows a flowchart of an exemplary clinical decision support process.

Various detailed embodiments of the present disclosure, taken in conjunction with the accompanying figures, are disclosed herein; however, it is to be understood that the disclosed embodiments are merely illustrative. In addition, each of the examples given in connection with the various embodiments of the present disclosure is intended to be illustrative, and not restrictive.

Throughout the specification, the following terms take the meanings explicitly associated herein, unless the context clearly dictates otherwise. The phrases "in one embodiment" and "in some embodiments" as used herein do not necessarily refer to the same embodiment(s), though it may. Furthermore, the phrases "in another embodiment" and "in some other embodiments" as used herein do not necessarily refer to a different embodiment, although it may. Thus, as described below, various embodiments may be readily combined, without departing from the scope or spirit of the present disclosure.

In addition, the term "based on" is not exclusive and allows for being based on additional factors not described, unless the context clearly dictates otherwise. In addition, throughout the specification, the meaning of "a," "an," and "the" include plural references. The meaning of "in" includes "in" and "on."

It is understood that at least one aspect/functionality of various embodiments described herein can be performed in real-time and/or dynamically. As used herein, the term "real-time" is directed to an event/action that can occur instantaneously or almost instantaneously in time when another event/action has occurred. For example, the "real-time processing," "real-time computation," and "real-time execution" all pertain to the performance of a computation during the actual time that the related physical process (e.g., a user interacting with an application on a mobile device) occurs, in order that results of the computation can be used in guiding the physical process.

As used herein, the term "dynamically" and term "automatically," and their logical and/or linguistic relatives and/or derivatives, mean that certain events and/or actions can be triggered and/or occur without any human intervention. In some embodiments, events and/or actions in accordance with the present disclosure can be in real-time and/or based on a predetermined periodicity of at least one of: nanosecond, several nanoseconds, millisecond, several milliseconds, second, several seconds, minute, several minutes, hourly, several hours, daily, several days, weekly, monthly, etc.

The exemplary embodiments relate to systems and methods configured to receive data describing the condition of an expectant mother, such as maternal heart rate data, fetal heart rate data, and uterine activity (e.g., contraction) data, perform a remote non-stress test on such data, and provide clinical decision support to a clinician on the basis of such a non-stress test. Some embodiments of the disclosure may be understood by referring, in part, to the following description and the accompanying drawings, in which like reference numbers refer to the same or like parts. In some embodiments, fetal heart rate is determined based at least on data obtained through the use of sensors (e.g., bio-potential sensors, acoustic sensors) integrated into at least one garment (e.g., a belt) worn by an expectant mother in accordance with one of the techniques described in U.S. Pat. No. 9,572,504, the contents of which are incorporated herein by reference in their entirety. In some embodiments, uterine activity is determined based at least on data obtained through the use of sensors (e.g., bio-potential sensors, acoustic sensors) integrated into at least one garment (e.g., a belt) worn by an expectant mother in accordance with one of the techniques described in U.S. Patent Application Publication No. 2021/0267535, the contents of which are incorporated herein by reference in their entirety.

In some embodiments, an analysis is performed in two stages. In some embodiments, in a first stage, basic clinical phenomena (e.g., heart rate accelerations or decelerations) are calculated with some level of confidence and marked on top of a fetal heart rate ("FHR") trace. In some embodiments, in a second stage, these basic phenomena are used to determine meaningful clinical decisions which are presented to the physicians.

In some embodiments, a first stage includes capturing fundamental clinical phenomena on the FHR trace utilizing analysis relating including digital signal processing ("DSP") and machine learning ("ML"), and presenting such clinical phenomena to a clinician. In some embodiments, the first stage includes a first sub-stage of capturing events and outputting features of such events, and a second sub-stage of filtering and presenting such events.

In some embodiments, events are captured utilizing an iterative process for estimating FHR baseline, and for identifying FHR baseline variability, capturing FHR accelerations and decelerations, and classifying such events into sub-types. FIG. 1 shows a flowchart of an exemplary iterative method 100 (e.g., iterative process). In step 110, a time window of relevant data (e.g., FHR data, MHR data, and contraction data) is received. In some embodiments, the data received in step 110 is referred to as an "input data set." In some embodiments, the window is 10 minutes in length. In some embodiments, when the method begins, the time window is a first time window, and subsequently the window is a subsequent time window. In some embodiments, each time window does not overlap adjacent time windows (e.g., the immediately preceding time window and the immediately following time window). In some embodiments, each time window overlaps the adjacent time windows. In some embodiments, adjacent time windows overlap each other by 5% of the duration of each time window (e.g., each time window is ten minutes in duration, and the amount of overlap is one half of one minute), or by 10% of the duration of each time window, or by 15% of the duration of each time window, or by 20% of the duration of each time window, or by 25% of the duration of each time window, or by 30% of the duration of each time window, or by 35% of the duration of each time window, or by 40% of the duration of each time window, or by 45% of the duration of each time window, or by 50% of the duration of each time window, or by 55% of the duration of each time window, or by 60% of the duration of each time window, or by 65% of the duration of each time window, or by 70% of the duration of each time window, or by 75% of the duration of each time window, or by 80% of the duration of each time window, or by 85% of the duration of each time window, or by 90% of the duration of each time window, or by 95% of the duration of each time window, or by a portion of each time window that is between 5% and 95% of the duration of each time window, or by any other amount that is between an overlap that is one data point in duration to an overlap that is an entire time window other than one non-overlapping data point.

In step 120, it is determined whether the time window includes a valid segment of data. In some embodiments, determination of validity is performed in accordance with the method 200 described hereinafter. If no valid data segment is found, the method returns to step 110 and a next window of data is received. If a valid data segment is found, the method continues to step 130.

In step 130, missing data samples are imputed on the input data set (e.g., the input data set is completed). In some embodiments, missing samples are imputed by interpolation. In some embodiments, interpolation is performed using a bi-directional auto-regressive interpolation model. In some embodiments, the result of completing the input data set in step 130 is referred to as a "completed data set." Following step 130, the method proceeds to step 140. In step 140, certain types of data are removed from the completed data set based on at least one criterion. In some embodiments, the criteria for the data removal of step 140 includes removing data representing periodic or episodic changes of FHR. In some embodiments, the criteria for the data removal of step 140 includes removing data representing periods of marked FHR variability. In some embodiments, the criteria for the data removal of step 140 includes removing segments of baseline FHR that differ by more than 25 beats per minute. In some embodiments, the criteria for the data removal of step 140 includes removing periodic or episodic changes by performing a moving average smoothing process, followed by applying a median±two standard deviations threshold. In some embodiments, marked variability and segments of baseline FHR that differ by more than 25 beats per minute are removed by identifying and removing segments of baseline FHR having consecutive samples that differ by more than 25 beats per minute. In some embodiments, the result of the data removal in step 140 is referred to as a "corrected data set."

Following step 140, in step 150, baseline FHR is determined (e.g., calculated). In some embodiments, following the removal of step 140, baseline is extracted from the original signal without the removed segments (e.g., from the corrected data set that is the result of step 140). In some embodiments, baseline FHR is determined in accordance with the method 300 that will be discussed hereinafter. In some embodiments, baseline FHR is determined as a computational baseline. In some embodiments, baseline FHR is determined using ACOG guidelines as the average of valid samples within a given time window. In step 160, accelerations and decelerations are identified. In some embodiments, accelerations are identified in accordance with the method 400 that will be described hereinafter. In some embodiments, decelerations are identified in accordance with the method 600 that will be described hereinafter.

In step 170, it is determined whether steps 140, 150, and 160 have been performed on a first iteration or a second iteration for the current data. If the first iteration has been completed, the method returns to step 140 and steps 140, 150, and 160 are repeated as described above. If the second iteration has been completed, the method continues to step 180. In step 180, the events identified in step 160 are classified (e.g., as the particular types of accelerations, the particular types of decelerations, or baseline changes) as described herein. Following step 180, in step 190, FHR variability is calculated. In some embodiments, variability is calculated in accordance with the method 500 described hereinafter. Following step 190, the method returns to step 110 and a next window of data is received.

Figure 2:
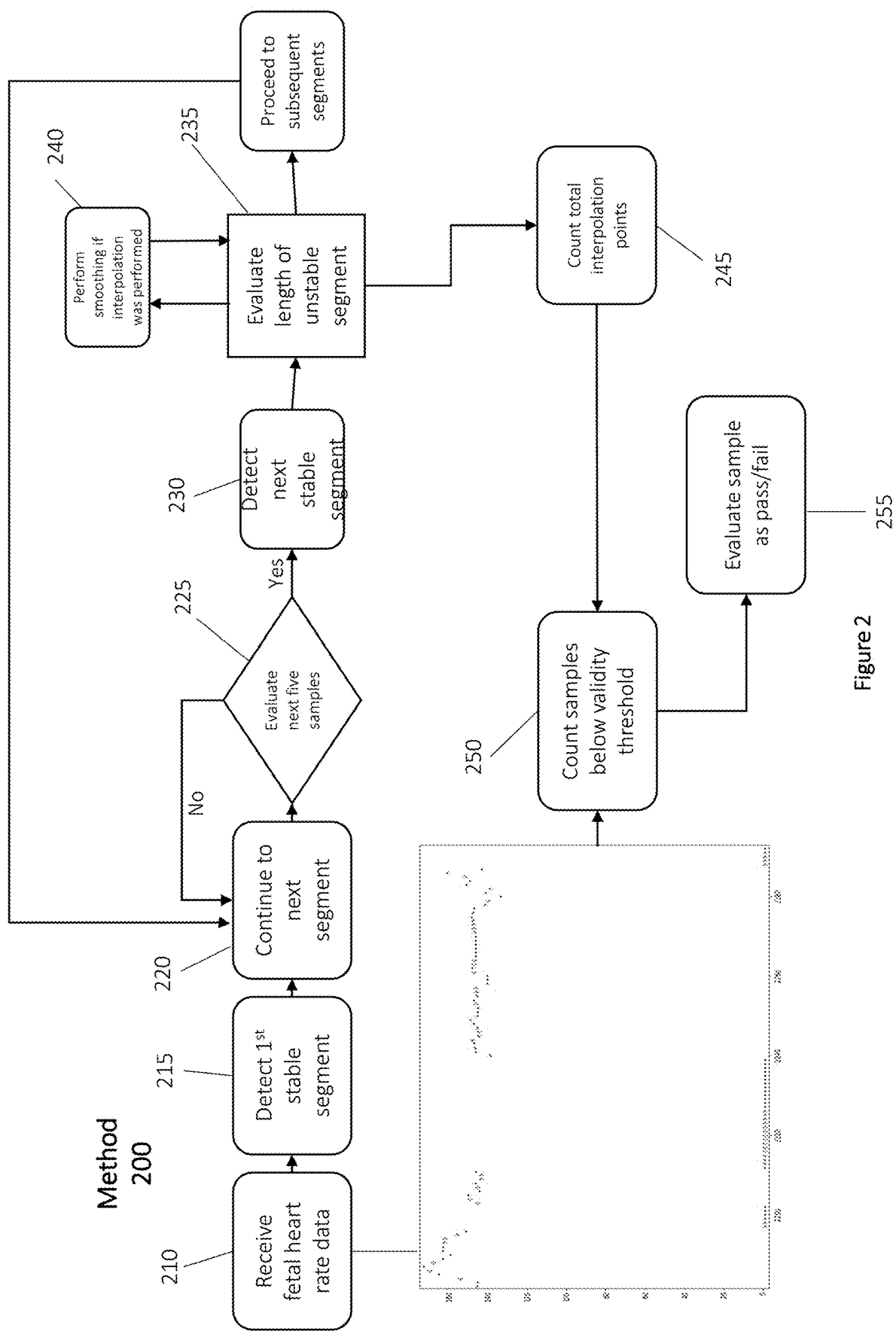
FIG. 2 shows a flowchart of an exemplary process for identifying a next valid fetal heart rate (FHR) data segment.

In some embodiments, the iterative process shown in FIG. 1 includes identifying a next valid segment of a FHR trace. FIG. 2 shows a flowchart of an exemplary method 200 for identifying a next valid segment. In step 210, a FHR session is received as input. In step 215, a first stable segment of the FHR session is detected. In some embodiments, a stable segment is a sequence of five adjacent samples (e.g., a predetermined quantity of consecutive samples) having a difference of FHR that is less than 25 bpm. In step 220, the method continues forward through the FHR session to a next segment. In step 225, the method determines whether the next segment includes five adjacent samples with a FHR difference that is greater than 25 bpm. If the segment does not include five adjacent samples with a FHR difference that is greater than 25 BPM, then the method returns to step 220. If the segment includes five adjacent samples with a FHR difference greater than 25 bpm, then the method continues to step 230.

In step 230, the method proceeds forward through the session to the next stable segment. In some embodiments, as in step 215, a stable segment is a sequence of five adjacent samples having a difference of FHR that is less than 25 bpm. In step 235, the length of the unstable segment (e.g., the length of time between the stable segment identified in step 230 and the prior stable segment) is evaluated. If the length is less than a threshold length, then interpolation is conducted to generate replacement FHR data for the unstable segment. In some embodiments, the threshold length is 2.5 seconds. In some embodiments, the interpolation is spline interpolation. In some embodiments, the interpolation is second order polynomial interpolation. Additionally, the number of samples in the unstable segment is counted. If the length of the unstable segment is greater than the threshold length, then no interpolation is performed, and the number of samples in the unstable segment is counted. In some embodiments, if interpolation has been performed, then the method proceeds to step 240. In step 240, a smoothing process is performed at the edges of the interpolated segment.

Following step 235, if the entire session has not yet been evaluated, then the method returns to step 215 and continues moving through the samples within the session and evaluating further segments of the session. If the entire session has been evaluated, then the method proceeds to step 245.

In step 245, the total number of interpolation points is counted as a trace quality metric. In parallel with step 245, in step 250, the total number of samples within the session having a BPM below a minimum valid BPM threshold M is counted. In some embodiments, the minimum valid BPM threshold M is 50 bpm. In some embodiments, samples having BPM below the minimum valid BPM threshold M are converted to invalid samples. In step 255, the sample is evaluated on a pass/fail basis based on constant thresholds for certain parameters. In some embodiments, the parameters include percentage of signal loss. In some embodiments, a threshold for percentage of signal loss is 40%. In some embodiments, the parameters include a confidence level for interpolated points. In some embodiments, the confidence level for interpolated points is +1 bpm.

In some embodiments, the parameters include a minimum number of stable minutes per sample. In some embodiments, the minimum number of stable minutes is two minutes per ten-minute sample. In some embodiments, a single stable segment of minimum length is sufficient.

In some embodiments, as a result of the process above, and in compliance with European College of Obstetrics and Gynaecology (ECOG) guidelines, there must be two stable minutes within a ten-minute sample to define a FHR baseline. In some embodiments, if this is not the case, then the baseline is indeterminate for a current sample. In some embodiments, if there is an indeterminate sample, then a previous frame is referred to in order to determine baseline FHR.

Figure 3:
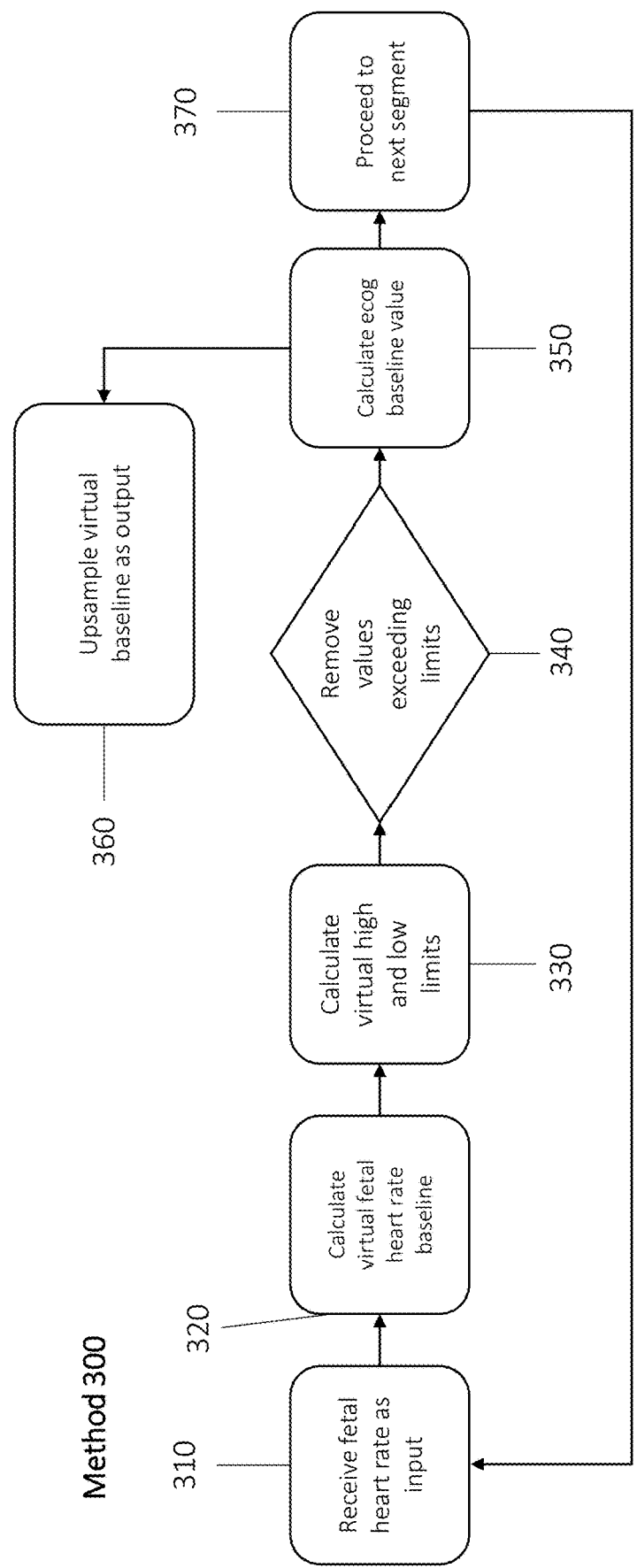
FIG. 3 shows a flowchart of an exemplary process for estimating FHR baseline.

In some embodiments, the iterative process shown in FIG. 1 includes estimating a baseline FHR for a given segment of an FHR trace. FIG. 3 shows a flowchart of an exemplary method 300 for estimating a baseline FHR. In step 310, a session of FHR data is received. In step 320, a virtual baseline R(n) is calculated. In some embodiments, the virtual baseline R(n) is calculated in accordance with the expression below (e.g., as an arithmetic mean average of all FHR data points):

$$R(n) = \frac{1}{N}\sum_{i=1}^{N} FHR(i)$$

In some embodiments, the virtual baseline R(n) is calculated over a 10-minute time window including 2400 FHR samples. In some embodiments, the virtual baseline R(n) is calculated using a moving median window two minutes in length with a one-minute overlap.

In step 330, virtual high and low FHR limits are calculated. In some embodiments, the virtual high and low FHR limits are calculated using a parameter a. In some embodiments, a is equal to two times the standard deviation of the virtual baseline R(n). In some embodiments, the virtual high FHR limit is calculated as R(n)+a and the virtual low FHR limit is calculated as R(n)−a. In step 340, outlier data points having FHR higher than the virtual high FHR limit or having FHR lower than the virtual low FHR limit are removed from the data set.

In step 350, an ecog baseline is calculated. In some embodiments, the ecog baseline is a 5 bpm rounded baseline of the calculated baseline. In some embodiments, the baseline is the mean FHR remaining in the sample after outlier data points are removed in step 340. In step 360, the virtual baseline is upsampled, with the first and last segments extrapolated, and is removed from the FHR trace. The output of step 360 is used as input for acceleration and deceleration extraction, which will be described hereinafter. In step 370, the method proceeds to the next segment. In some embodiments, each subsequent segment has a two-minute overlap with the preceding segment.

In some embodiments, the iterative process shown in FIG. 1 includes extracting (e.g., identifying) FHR accelerations, including identifying prolonged accelerations and baseline changes based on identified FHR accelerations. In some embodiments, a FHR acceleration is a visually apparent abrupt increase in FHR. In some embodiments, an increase is an abrupt increase if less than 30 seconds elapse between the onset of the increase and the peak FHR. In some embodiments, after 32 weeks of gestation, an acceleration has a peak of 15 bpm or more above the baseline FHR, and a duration of between 15 seconds and two minutes between onset and return to baseline. In some embodiments, before 32 weeks of gestation, an acceleration has a peak of 10 bpm or more above the baseline FHR, and a duration of between 10 seconds and two minutes between onset and return to baseline. In some embodiments, a prolonged acceleration has a duration of between two minutes and ten minutes. In some embodiments, if an acceleration lasts for longer than ten minutes, it is considered to be a change in baseline FHR.

Figure 4:
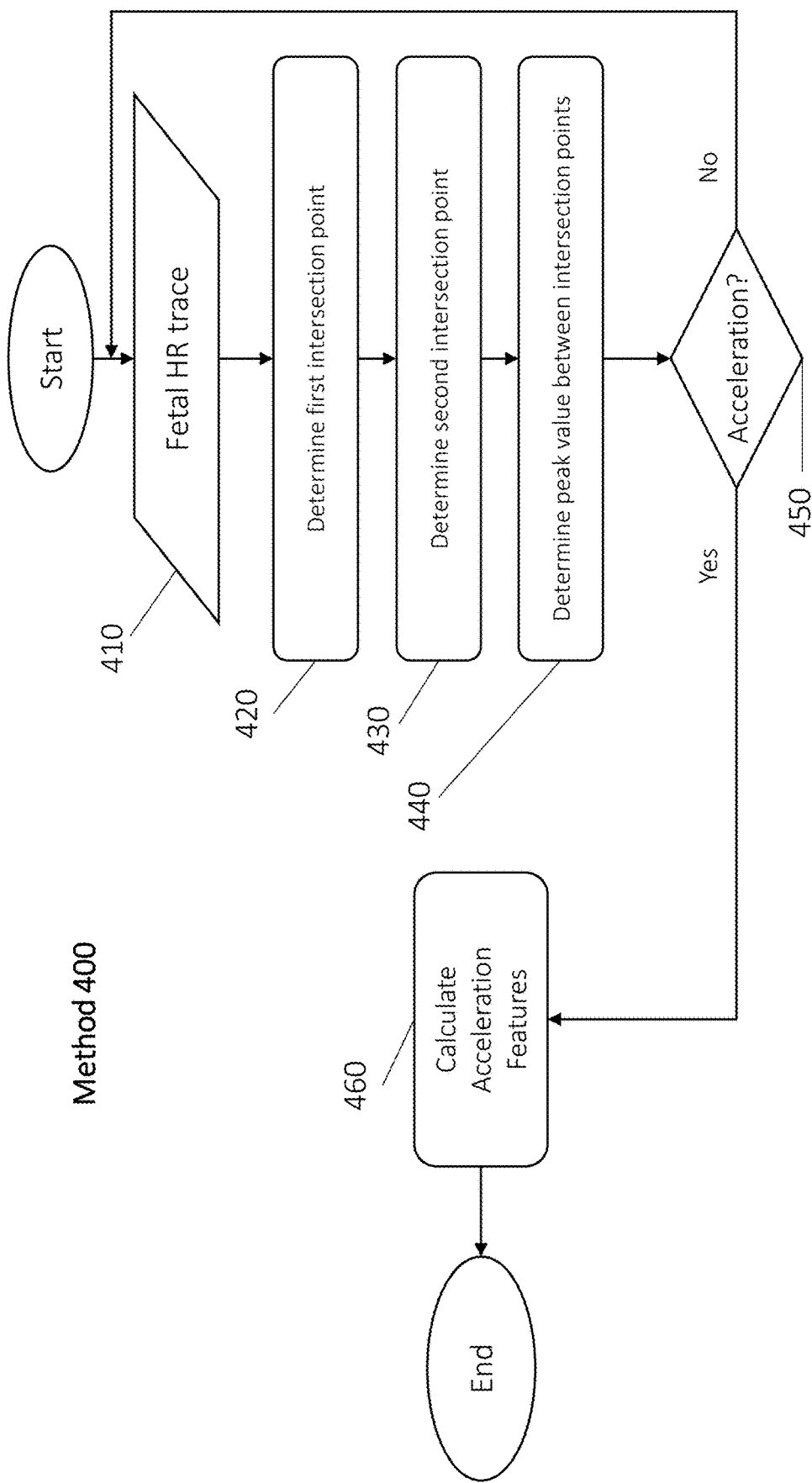
FIG. 4 shows a flowchart of an exemplary process for identifying FHR accelerations.

FIG. 4 shows a flowchart of an exemplary method 400 for extracting FHR accelerations. In step 410, the method receives a FHR trace as input. In step 420, a first intersection X1 between the baseline FHR and the FHR trace is identified. In step 430, a second intersection X2 between the baseline FHR and the FHR trace is identified. In step 440, a peak FHR Ymax of the FHR trace between X1 and X2 is determined.

In step 450, it is determined whether the period between X1 and X2 is considered to be an acceleration. In some embodiments, for an expectant mother at less than 32 weeks of gestation, a period is considered to be an acceleration if (a) the elapsed time period between X1 and X2 is greater than or equal to 10 seconds, (b) the increase in FHR from the baseline FHR to the peak FHR Ymax is greater than or equal to 10 bpm, and (c) the time elapsed between the potential onset X1 and the time of the peak FHR Ymax is less than or equal to 30 seconds. In some embodiments, for an expectant mother at greater than or equal to than 32 weeks of gestation, a period is considered to be an acceleration if (a) the elapsed time period between X1 and X2 is greater than or equal to 15 seconds, (b) the increase in FHR from the baseline FHR to the peak FHR Ymax is greater than or equal to 15 bpm, and (c) the time elapsed between the potential onset X1 and the time of the peak FHR Ymax is less than or equal to 30 seconds. Following step 450, if the period between X1 and X2 is not considered to be an acceleration, the method returns to step 410 and a next period is considered. If the period is considered to be an acceleration, the method continues to step 460.

In step 460, features of the acceleration are calculated. In some embodiments, if the elapsed time between X1 and X2 is greater than or equal to ten minutes, the acceleration is considered to be a change in baseline FHR. In some embodiments, if the elapsed time between X1 and X2 is greater than or equal to two minutes, but less than ten minutes, the acceleration is considered to be a prolonged acceleration. Following step 460, the method 400 is completed for a given acceleration, and is performed again for subsequent potential accelerations.

Figure 5:
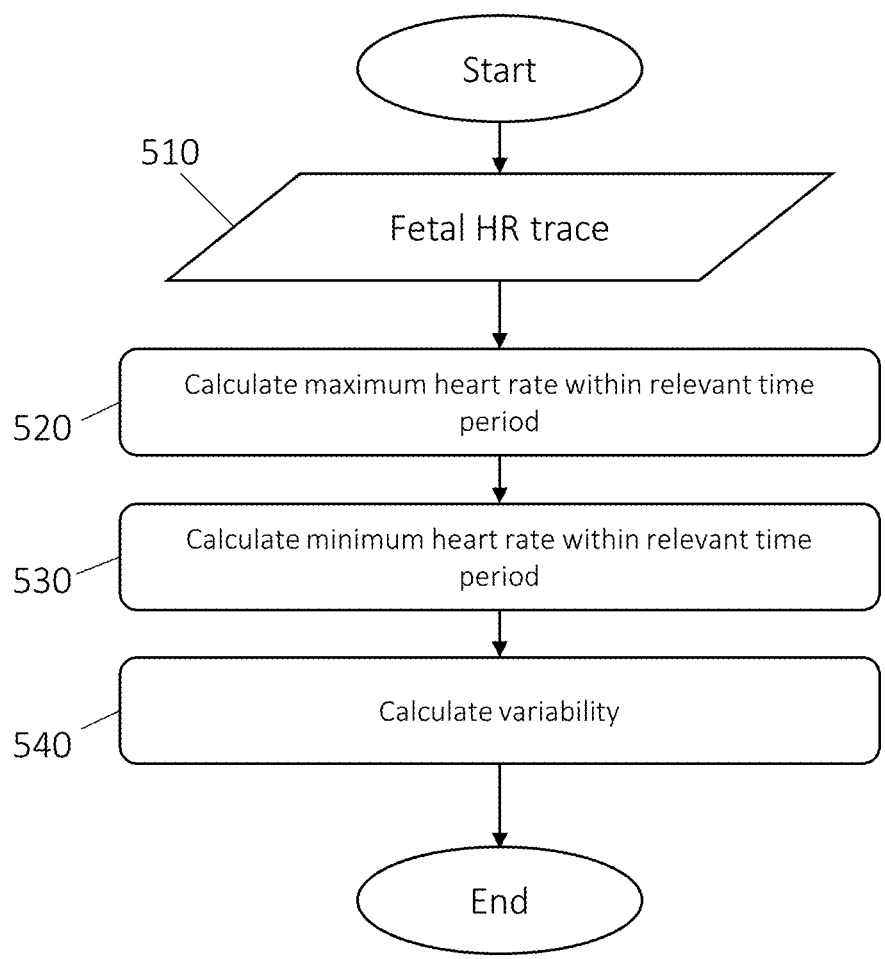
FIG. 5 shows a flowchart of an exemplary process for extracting FHR baseline variability.

In some embodiments, the iterative process shown in FIG. 1 includes extracting FHR baseline variability. FIG. 5 shows a flowchart of an exemplary method 500 for extracting FHR baseline variability. In step 510, an FHR trace is received. In step 520, a highest FHR value Ymax is calculated for a time period that is within two minutes after a point X2. and before any subsequent acceleration or deceleration. In step 530, a lowest FHR value Ymin is calculated for the same time period that is within two minutes after a point X2 and before any subsequent acceleration or deceleration. In step 540, the variability is calculated by subtracting Ymax-Ymin. In some embodiments, variability is calculated on the FHR trace for each two-minute period on segments that are between identified accelerations and decelerations.

Figure 6:
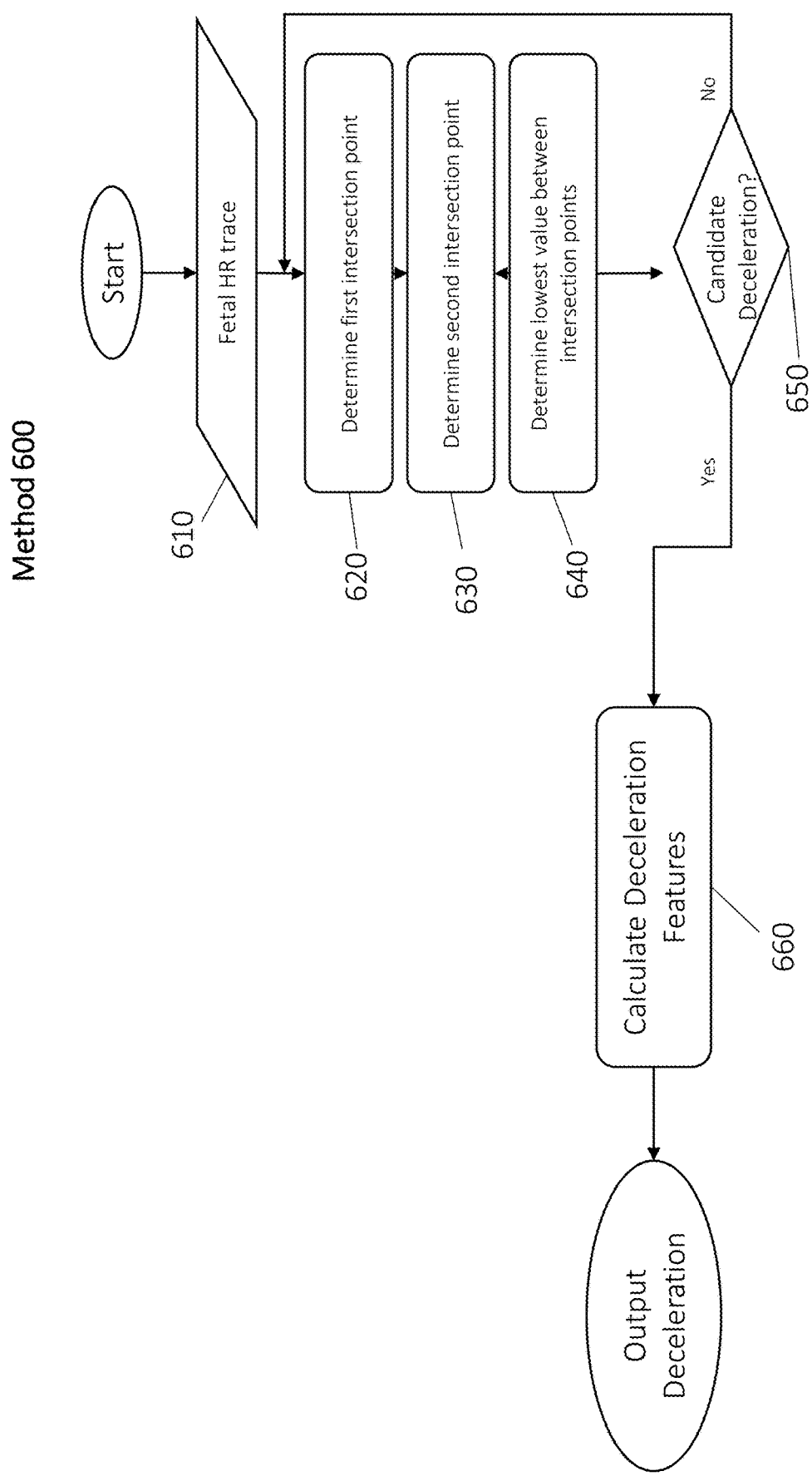
FIG. 6A shows a flowchart of an exemplary process for identifying FHR decelerations.
FIG. 6B shows an exemplary chart of fetal heart rate and uterine contractions.
Figure 6B:
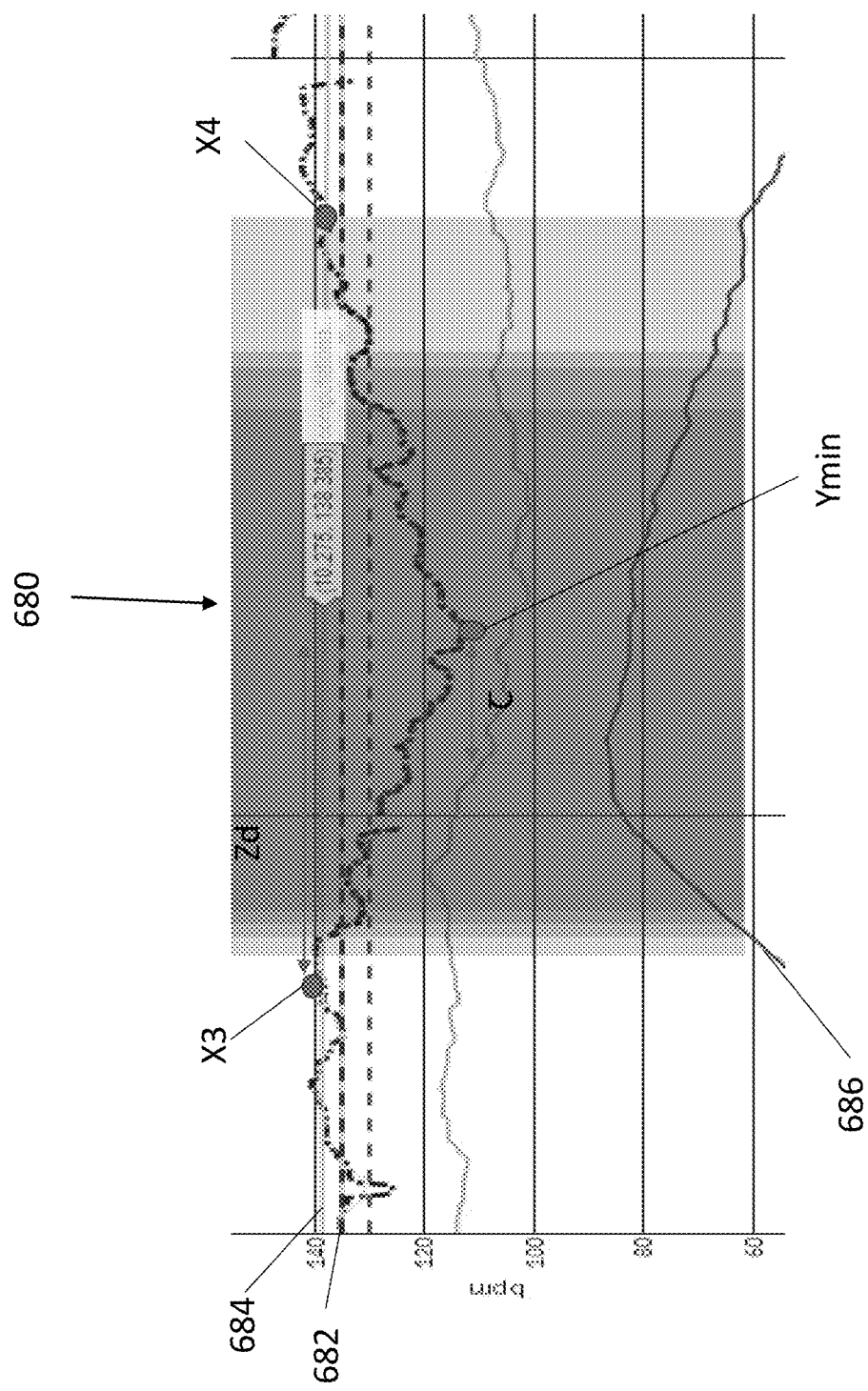

In some embodiments, the iterative process shown in FIG. 1 includes extracting FHR decelerations. FIG. 6A shows a flowchart of an exemplary method 600 for extracting FHR decelerations, and FIG. 6B shows a graph 680 of a fetal heart rate signal 682, a fetal heart rate baseline 684, a uterine activity signal 686, and other points as will be described hereinafter. In step 610, an FHR trace is received as input. In step 620, a first intersection point X3 between the baseline FHR and the FHR trace is identified. In step 630, a subsequent second intersection point X4 between the baseline FHR and the FHR trace is identified. In step 640, a lowest value Ymin of the FHR trace during the period between X3 and X4 is calculated. In step 650, it is determined whether the period between X3 and X4 is a candidate deceleration. In some embodiments, the period between X3 and X4 is identified as a candidate deceleration if the lowest FHR between X3 and X4 is at least 15 bpm less than the baseline FHR. In step 660, features of the deceleration are calculated. In some embodiments, features calculated for decelerations include fall time (e.g., duration from onset to nadir), slope from onset to nadir, rise time (e.g., duration from nadir to offset), and slope from nadir to offset. In step 670, the deceleration is output as a candidate deceleration.

In some embodiments, the iterative process shown in FIG. 1 includes classifying FHR decelerations that have been extracted. For example, in some embodiments, a FHR deceleration may be classified as an early deceleration. In some embodiments, an early deceleration is a visually apparent and usually symmetrical gradual decrease and return of FHR associated with a uterine contraction. In some embodiments, a gradual decrease is defined as having an elapsed time of 30 seconds or more between onset of the deceleration and the nadir of the deceleration (e.g., the minimum FHR during the deceleration). In some embodiments, the magnitude of the decrease is measured from the onset to the nadir. During an early deceleration, the nadir occurs at the same time as the peak of an associated uterine contraction. In most cases, the onset, nadir, and recovery of the deceleration coincide with the beginning, peak, and ending, respectively, of an associated uterine contraction.

In some embodiments, a FHR deceleration may be classified as a late deceleration. In some embodiments, a late deceleration is a visually apparent and usually symmetrical gradual decrease and return of FHR associated with a uterine contraction. In some embodiments, a gradual decrease is defined as having an elapsed time of 30 seconds or more between onset of the deceleration and the nadir of the deceleration (e.g., the minimum FHR during the deceleration). In some embodiments, the magnitude of the decrease is measured from the onset to the nadir. During a late deceleration, the nadir occurs after the peak of an associated uterine contraction. In most cases, the onset, nadir, and recovery of the deceleration occur after the beginning, peak, and ending, respectively, of an associated uterine contraction.

In some embodiments, a FHR deceleration may be classified as a variable deceleration. In some embodiments, a variable deceleration is a visually apparent abrupt decrease in FHR. In some embodiments, an abrupt decrease in FHR is defined as having an elapsed time of less than 30 seconds between onset of the deceleration and the nadir of the deceleration (e.g., the minimum FHR during the deceleration). In some embodiments, the magnitude of the decrease is measured from the onset to the nadir. In some embodiments, a variable deceleration is defined as having a decrease in FHR of 15 beats per minute or more, and having a duration of between 15 seconds and two minutes. When variable decelerations are associated with uterine contractions, their onset, depth, and duration commonly vary among successive uterine contractions.

In some embodiments, a FHR deceleration may be classified as a prolonged deceleration. In some embodiments, a prolonged deceleration is a visually apparent decrease in FHR below the baseline FHR. In some embodiments, a prolonged deceleration is defined as having a decrease in FHR of 15 beats per minute or more, and having a duration of between two minutes and ten minutes. In some embodiments, a decrease in FHR that lasts for longer than ten minutes is considered to be a change in baseline FHR.

Figure 7:
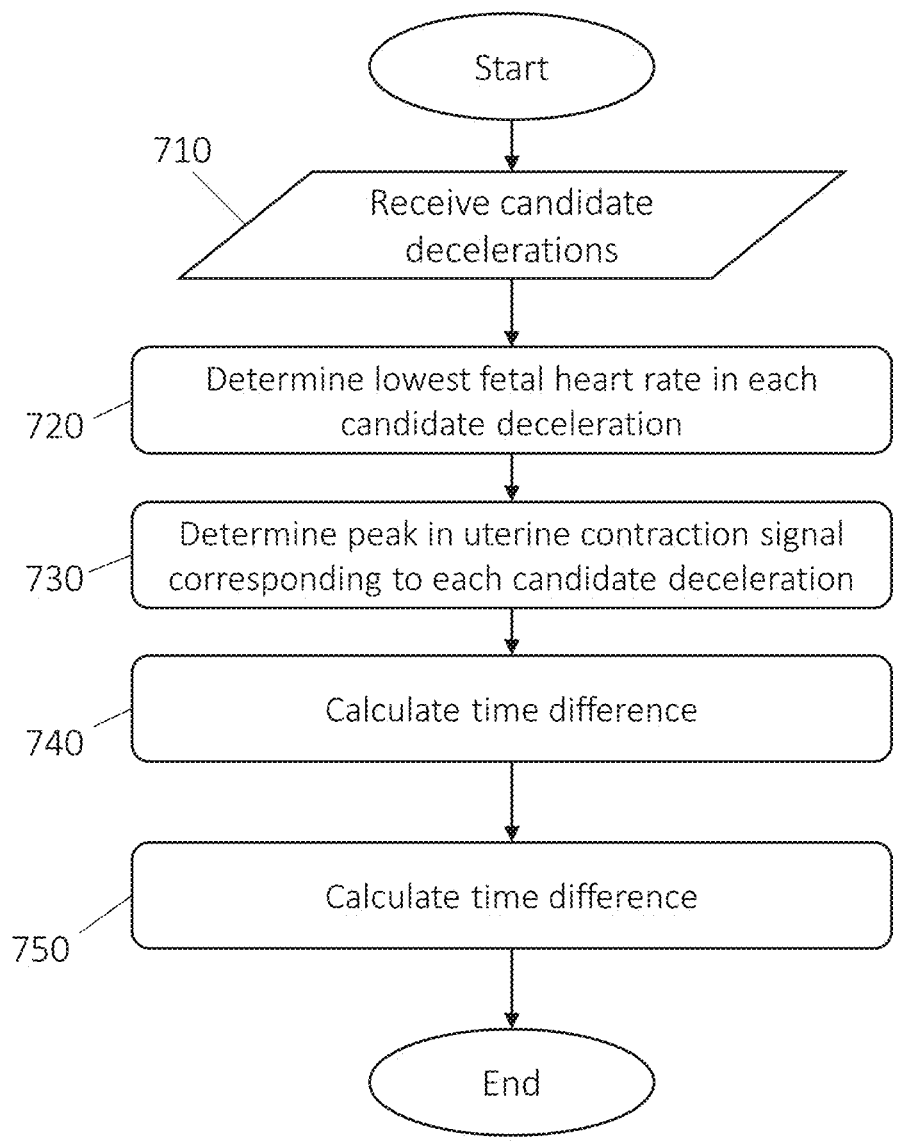
FIG. 7 shows a flowchart of an exemplary process for classifying FHR decelerations.

FIG. 7 shows a flowchart of an exemplary method 700 for classifying FHR decelerations (e.g., as early decelerations, late decelerations, variable decelerations, or prolonged decelerations, as defined above). In step 710, candidate decelerations (e.g., the output of method 600) are received as input. In step 720, for each candidate deceleration, a lowest FHR value Ymin is identified, and a delay Zd is calculated as the time elapsed between the onset X3 and the time of the first occurrence of Ymin. In step 730, for each candidate deceleration, a peak in a uterine contraction signal UCmax is identified and correlated with the candidate deceleration. In step 740, for each candidate deceleration, a time difference t (see FIG. 6B) is calculated as the difference between the time of the nadir of the candidate deceleration and the time of the peak of the correlated uterine contraction.

In step 750, each candidate deceleration is classified based on the delay Zd and based on a comparison of the time difference t to the correlated uterine contraction duration. In some embodiments, if (a) t is less than or equal to half the uterine contraction plus or minus five seconds, (b) t is greater than zero, and (c) the delay Zd is greater than 30 seconds, then the candidate deceleration is classified as a late deceleration. In some embodiments, if (a) t is less than or equal to half the uterine contraction plus or minus five seconds, (b) t is less than zero, and (c) the delay Zd is greater than 30 seconds, then the candidate deceleration is classified as an early deceleration. In some embodiments, if (a) t is greater than half the uterine contraction plus or minus five seconds, (b) the total duration of the candidate deceleration is less than or equal to 600 seconds, and (c) the delay Zd is between 15 seconds and 30 seconds, then the candidate deceleration is classified as a prolonged deceleration. In some embodiments, if (a) the total duration of the candidate deceleration is less than or equal to 120 seconds, and (b) the delay Zd is between 15 seconds and 30 seconds, then the candidate deceleration is classified as a variable deceleration.

In some embodiments, on the basis of the performance of step 750, an elongated deceleration epoch alert is generated if a deceleration is identified having a total duration greater than one minute. In some embodiments, on the basis of the performance of step 750, a variable deceleration epoch alert is generated if three adjacent variable decelerations are identified within a 20-minute duration. Following step 750, the method 700 is complete.

In some embodiments, following performance of the iterative process shown in FIG. 1 on a given session, a marking service outputs an aggregated list of events. In some embodiments, each event in such an aggregated list includes morphological and temporal parameters. In some embodiments, each event includes an event description, and timing information such as start time, end time, peak time, rise time, and fall time. In some embodiments, each event (e.g., each acceleration and deceleration) is classified with a level of "clinical confidence" from high to low. In some embodiments, clinical confidence includes amplitude confidence and duration confidence. In some embodiments, amplitude confidence describes the confidence level of the event amplitude, defined as the relative distance between the event's maximum peak and the ACOG criteria for the event (e.g., the event's peak minus the ACOG criteria, divided by the ACOG criteria). In some embodiments, duration confidence describes the confidence level of the event duration, defined as the percentage shift between the event's maximum duration and the corresponding ACOG parameter, relatively to the ACOG parameter criteria (e.g., the event's duration minus the ACOG parameter, divided by the ACOG parameter). To provide an illustrative example using numerical values selected for clarity of illustration, for a given event type, the ACOG guidelines may define a threshold value of 10 bpm, and the detected candidate event may have a value of 13 bpm. In such an example, the clinical amplitude confidence is equal to ((13−10)/10)=0.3. As another example, the ACOG guidelines may define a threshold value of 10 bpm, and the detected candidate event may have a value of 16 bpm. In such an example, the clinical amplitude confidence is equal to ((16−10)/10)=0.6. For this type of confidence, a higher confidence value indicates a higher degree of certainty in the event (e.g., if the ACOG criteria define a deceleration as having a threshold value of 10 bpm and a detected candidate event has 16 bpm, the confidence value of 0.6 indicates a higher degree of certainty that a deceleration has occurred than would a confidence value of 0.3).

In some embodiments, a user interface allows a clinician to select a threshold confidence level and to display only events meeting the selected threshold. In some embodiments, each event (e.g., each acceleration and deceleration) is classified with a level of "algorithmic confidence" representing the level of confidence of the process described above that the event exists based on internal factors. In some embodiments, the algorithmic confidence for each event is defined as the average of the square root of the distance between the upper and lower confidence intervals (e.g., 95% confidence interval) of any imputed (e.g., interpolated) samples within the event's continuous segments. To provide an illustrative example using numerical values selected for clarity of illustration, a given interpolated data point may have a predicted value of 144 bpm with an upper 95% confidence interval of 146 bpm and a lower 95% confidence interval of 142 bpm. In this case, the confidence interval is 4 bpm (e.g., 146 bpm-142 bpm). If a data point is not interpolated, its confidence interval is zero. To generate an algorithmic confidence of an event, the square root of the confidence interval of each data point within the event is averaged. For example, if an event has 8 data points having confidence intervals of 0, 0, 0, 1, 4, 1, 0, 0, then the square roots of the 8 confidence intervals 0, 0, 0, 1, 2, 1, 0, 0 are averaged (0+0+0+1+2+1+0+0)/8 to produce an algorithmic confidence of 0.5 for the event. Thus, if there are no imputed samples between the onset and offset of the event, the algorithmic confidence value is zero. For this type of confidence, a higher confidence value indicates a higher degree of uncertainty in the event due to the inclusion of more interpolated data points and/or interpolated data points having larger 95% confidence intervals.

In some embodiments, events are filtered and presented. In some embodiments, events are filtered based on a set of predefined parameters for each event type. In some embodiments, the predefined parameters include values and confidence levels. In some embodiments, events that do not meet the predefined parameters are filtered out. In some embodiments, events that are not filtered out are provided to a clinician via a user interface such as marking the events on a FHR trace. In some embodiments, provision of results to the clinician completes the first stage of the analysis.

In some embodiments, in the second stage of the analysis, clinical phenomena captured in the first stage are analyzed and, based on this analysis, together with known clinical guidelines, clinical decisions are suggested to a clinician. In some embodiments, the second stage includes supporting basic decisions. In some embodiments, basic decisions include classifying a session as reactive or non-reactive. In some embodiments, a session is classified as reactive if at least two accelerations were detected during the first iteration. In some embodiments, basic decisions include classifying a session as normal, suspicious, or pathological. In some embodiments, a session is classified as normal, suspicious, or pathological based on whether each of the features of (a) the FHR baseline during the session, (b) the FHR variability during the session, (c) FHR decelerations during the session, and (d) FHR accelerations during the session are categorized as reassuring, non-reassuring, or abnormal. FIG. 8 shows a table defining exemplary criteria for defining the above parameters as either reassuring, non-reassuring, or abnormal. In some embodiments, a session is classified as normal if all four features fall into the reassuring category. In some embodiments, a session is classified as suspicious if one of the features falls into the non-reassuring category and the remaining features fall into the reassuring category. In some embodiments, a session is categorized as pathological if two or more of the features fall into the non-reassuring category, or if one or more of the features fall into the abnormal category.

In some embodiments, supporting basic decisions also includes providing alerts to a clinician based on non-reassuring conditions such as tachycardia. In some embodiments, alerts are provided based on baseline FHR. In some embodiments, an alert indicating tachycardia is provided if baseline FHR is greater than 160 bpm. In some embodiments, an alert indicating bradycardia is provided if baseline FHR is less than 110 bpm for at least ten minutes.

In some embodiments, alerts are provided based on FHR variability. In some embodiments, an alert indicating absent variability is provided if there is a persistent undetectable amplitude of range of the FHR of less than or equal to 5 bpm. In some embodiments, an alert indicating minimal variability is provided if there is an amplitude range that is detectable but less than or equal to 5 bpm. In some embodiments, an alert indicating marked variability is provided if FHR variability is greater than or equal to 25 bpm. In some embodiments, an alert indicating sinusoidal variability is provided if FHR baseline shows a sinusoidal pattern with a frequency of 3 to 5 cycles per minute that persists for at least 20 minutes.

In some embodiments, alerts are provided based on FHR accelerations. In some embodiments, an alert indicating prolonged acceleration is provided if an FHR acceleration is detected lasting between 2 minutes and 10 minutes. In some embodiments, an alert indicating a baseline shift is indicated if an FHR acceleration is detected lasting more than 10 minutes.

In some embodiments, alerts are provided based on FHR decelerations. In some embodiments, an alert indicating late deceleration is provided if an FHR deceleration is detected for which onset, nadir, and recovery of the FHR deceleration occur after the beginning, peak, and ending of an associated contraction, as discussed above. In some embodiments, an alert indicating a variable deceleration is provided if an FHR deceleration is detected that is an abrupt decrease below the baseline FHR. In some embodiments, a variable deceleration can be categorized as nonrepetitive and brief if lasting less than 20 seconds, or can be categorized as repetitive if at least three such decelerations occur over a 20-minute time period. In some embodiments, an alert indicating a prolonged deceleration is provided if an FHR deceleration is detected that is a gradual or abrupt decrease in FHR of over 15 bpm below the baseline FHR lasting at least two minutes between onset and return to baseline FHR. In some embodiments, alerts are provided based on associated FHR and maternal heart rate (MHR) patterns.

In some embodiments, the second stage includes supporting "advanced" decisions. In some embodiments, supporting advanced decisions includes providing a recommendation to continue a monitoring session. In some embodiments, supporting advanced decisions includes providing a recommendation to conduct a subsequent monitoring session. In some embodiments, a recommendation to continue a monitoring session is provided based on guidelines and the current findings. For example, in some embodiments, if two or more accelerations were not found during a first 20-minute monitoring session, a recommendation to continue monitoring for an additional 20 minutes is provided. In some embodiments, following such an additional 20-minute session, a reactive or non-reactive conclusion is provided. In some embodiments, a recommendation to conduct a subsequent monitoring session is provided based on a finding that the current monitoring session is uninterpretable and no decision can be provided.

In some embodiments, one or more exemplary processes described herein are performed locally (e.g., client-side) at a wearable device, e.g., using an onboard computing system of a wearable device. In some embodiments, one or more exemplary processes described herein are performed remotely from a wearable device, e.g., at a remote server, using cloud computing, etc. In some embodiments, an applicable computing system may include hardware components such as a processor, which may include local or remote processing components. In some embodiments, the processor may include any type of data processing capacity, such as a hardware logic circuit, for example an application specific integrated circuit (ASIC) and a programmable logic, or such as a computing device, for example, a microcomputer or microcontroller that include a programmable microprocessor. In some embodiments, the processor may include data-processing capacity provided by the microprocessor. In some embodiments, the microprocessor may include memory, processing, interface resources, controllers, and counters. In some embodiments, the microprocessor may also include one or more programs stored in memory.

In some embodiments, a relevant computing system may include one or more computer devices implemented as a local or on-premises computing system, a cloud computing system or hybrid cloud computing system having one or more hardware and/or software components located in a cloud computing system and one or more hardware and/or software components located in a local computing system. In some embodiments, "cloud," "Internet cloud," "cloud computing," "cloud architecture," and similar terms may include at least one of the following: (1) a large number of computers connected through a real-time communication network (e.g., Internet); (2) providing the ability to run a program or application on many connected computers (e.g., physical machines, virtual machines (VMs)) at the same time; (3) network-based services, which appear to be provided by real server hardware, and are in fact served up by virtual hardware (e.g., virtual servers), simulated by software running on one or more real machines (e.g., allowing to be moved around and scaled up (or down) on the fly without affecting the end user). The aforementioned examples are, of course, illustrative and not restrictive.

Similarly, a computing system may include storage, such as one or more local and/or remote data storage solutions such as, e.g., local hard-drive, solid-state drive, flash drive, database or other local data storage solutions or any combination thereof, and/or remote data storage solutions such as a server, mainframe, database or cloud services, distributed database or other suitable data storage solutions or any combination thereof. In some embodiments, the storage may include, e.g., a suitable non-transient computer readable medium such as, e.g., random access memory (RAM), read only memory (ROM), one or more buffers and/or caches, among other memory devices or any combination thereof.

In some embodiments, an exemplary computing system may implement a computer engine to perform any of the processes described herein. In some embodiments, the terms "computer engine" and "engine" identify at least one software component and/or a combination of at least one software component and at least one hardware component which are designed/programmed/configured to manage/control other software and/or hardware components (such as the libraries, software development kits (SDKs), objects, etc.).

Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. In some embodiments, the one or more processors may be implemented as a Complex Instruction Set Computer (CISC) or Reduced Instruction Set Computer (RISC) processors; x86 instruction set compatible processors, multi-core, or any other microprocessor or central processing unit (CPU). In various implementations, the one or more processors may be dual-core processor(s), dual-core mobile processor(s), and so forth.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some embodiments, a system includes a non-transient computer memory storing software instructions; and at least one computer processor configured, when executing the software instructions, to: receive an input data set for an expectant mother during a time window, wherein the input data set includes at least fetal heart rate data, wherein the fetal heart rate data is calculated based at least on raw bio-potential data obtained by a plurality of bio-potential sensors in a garment worn by the expectant mother; complete the input data set with at least one missing data sample to provide a completed data set; remove at least one segment from the completed data set based on at least one criterion to provide a corrected data set; calculate a baseline fetal heart rate based at least on the corrected data set; detect at least one event occurring during the time window based at least on at least one of the corrected data set or the baseline fetal heart rate; classify the at least one event as either an acceleration, a deceleration, or a baseline change based at least on at least one of the corrected data set or the baseline fetal heart rate; and generate an output indicative of at least the at least one event, wherein the output is configured to enable at least one action being taken with respect to the expectant mother.

In some embodiments, the at least one criterion for removing the at least one segment from the completed data set includes removing the at least one segment based on the at least one segment including a periodic change in the fetal heart rate. In some embodiments, the periodic change in the fetal heart rate includes at least one of (a) the fetal heart rate varying by more than 25 beats per minute in consecutive samples or (b) applying a threshold based on median and standard deviation.

In some embodiments, the computer processor is further configured to determine whether the input data set is valid or is not valid; and if the input data set is determined to be not valid, receive a further input data set prior to completing the input data set, wherein the completing the input data set is performed on the further input data set. In some embodiments, the step of determining whether the input data set is valid or is not valid is performed by a process including: identifying a plurality of stable segments of the corrected data set, wherein each stable segment includes a sequence of a predetermined quantity of consecutive samples having a fetal heart rate variability that is less than a predetermined threshold variability; determining a total duration of the plurality of stable segments; and determining whether the input data set is valid or is not valid based at least on a comparison of the total duration of the plurality of stable segments to a predetermined threshold duration.

In some embodiments, determining the baseline fetal heart rate is performed by a process including: calculating a virtual baseline fetal heart rate; calculating a virtual high fetal heart rate limit; calculating a virtual low fetal heart rate limit; removing outlier data points from the corrected data set, wherein outlier data points are data points having a fetal heart rate higher than the virtual high fetal heart rate limit or having a fetal heart rate lower than the virtual low fetal heart rate limit; and calculating the baseline fetal heart rate based at least on applying rounding to the corrected data set following removing the outlier data points. In some embodiments, the virtual baseline fetal heart rate is a mean average of fetal heart rates in the corrected data set. In some embodiments, the steps of calculating the virtual high fetal heart rate limit and calculating the virtual low fetal heart rate limit are performed by a process including: calculating a standard deviation for the virtual baseline fetal heart rate; calculating the virtual high fetal heart rate limit as the virtual baseline fetal heart rate plus two times the standard deviation; and calculating the virtual low fetal heart rate limit as the virtual baseline fetal heart rate minus two times the standard deviation.

In some embodiments, at least one of the at least one event is classified as an acceleration, and the at least one of the at least one event is classified as an acceleration based on a process including: identifying a first intersection between a trace of the corrected data set and the baseline fetal heart rate; identifying a second intersection between the trace of the corrected data set and the baseline fetal heart rate; identifying a maximum fetal heart rate during a time interval between the first intersection and the second intersection; and identifying the time interval as including the acceleration based at least on a duration of the time interval and the maximum fetal heart rate during the time interval. In some embodiments, the step of identifying the time interval as including the acceleration is further based on a gestational week of the expectant mother. In some embodiments, a method also includes determining fetal heart rate baseline variability. In some embodiments, the step of determining the fetal heart rate baseline variability is performed by a process including: determining a highest fetal heart rate during a variability time interval following the second intersection, wherein the variability time interval extends from the second intersection until a sooner of (1) a predetermined duration following the second intersection or (2) onset of a subsequent acceleration or deceleration; determining a lowest fetal heart rate during the variability time interval; and subtracting the lowest fetal heart rate during the variability time interval from the highest fetal heart rate during the variability time interval to provide the fetal heart rate baseline variability.

In some embodiments, the at least one event includes a deceleration, and the at least one event is classified as a deceleration based on a process including: identifying a first intersection between a trace of the corrected data set and the baseline fetal heart rate; identifying a second intersection between the trace of the corrected data set and the baseline fetal heart rate; identifying a minimum fetal heart rate during a time interval between the first intersection and the second intersection; and identifying the time interval as including the deceleration based at least on a difference between the baseline fetal heart rate and the minimum fetal heart rate during the time interval. In some embodiments, a method also includes classifying the deceleration as one of an early deceleration, a late deceleration, a variable deceleration, or a prolonged deceleration. In some embodiments, the input data set also includes a uterine contraction signal, and the deceleration is classified as the one of the early deceleration, the late deceleration, the variable deceleration, or the prolonged deceleration based on a process including: determining a delay, wherein the delay is an amount of elapsed time between the first intersection and a time of the minimum fetal heart rate during the time interval; determining a time of a peak of a uterine contraction during the time interval; determining a time difference between the time of the minimum fetal heart rate during the time interval and the time of the peak of the uterine contraction signal during the time interval; and classifying the deceleration as the one of the early deceleration, the late deceleration, the variable deceleration, or the prolonged deceleration based at least on the delay, the time difference, and a duration of the uterine contraction.

In some embodiments, two iterations of the steps of (1) removing at least one segment from the completed data set based on at least one criterion to provide a corrected data set, (2) calculating a baseline fetal heart rate based at least on the corrected data set, and (3) detecting at least one event occurring during the time window based at least on at least one of the corrected data set or the baseline fetal heart rate, are performed for the time window.

In some embodiments, the computer processor is further configured to repeat, for a subsequent time window, the steps of: receiving an input data set for the expectant mother; completing the input data set with at least one missing data sample to provide a completed data set; removing at least one segment from the completed data set based on at least one criterion to provide a corrected data set a baseline fetal heart rate based at least on the corrected data set; detecting at least one event occurring during the time window based at least on at least one of the corrected data set or the baseline fetal heart rate; and classifying the at least one event as either an acceleration, a deceleration, or a baseline change based at least on at least one of the corrected data set or the baseline fetal heart rate. In some embodiments, the subsequent time window does not overlap the time window. In some embodiments, the subsequent time window overlaps the time window by an overlap duration. In some embodiments, the overlap duration is between 5% of a duration of the time window and 95% of the duration of the time window.

Study Results

A study was conducted in which expectant mothers with high-risk singleton pregnancies at 32 weeks of gestational age or more performed self-administered remote non-stress tests (NSTs) using the sensor-laden belt commercialized by Nuvo Group, Limited of Tel Aviv, Israel under the trade name INVU. Remote NSTs administered during the course of the study replaced in-clinic NSTs. The NSTs were reviewed by clinicians via a web application. The clinicians determined clinically interpretability and reactivity. Interpretable sessions were retrospectively analyzed by the clinical decision support system (CDSS) as described herein for reactivity and compared to clinician assessment. The average time to reach reactivity by the CDSS was compared to the average length of the NST sessions.

Figure 9A:
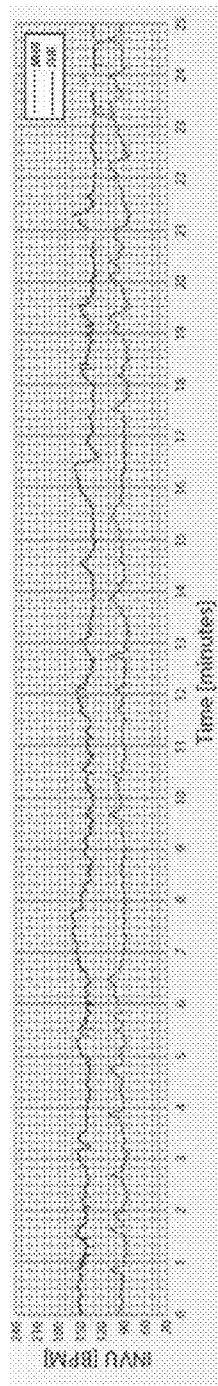
FIG. 9A shows output of an exemplary clinical decision support system for a first patient.
Figure 9B:
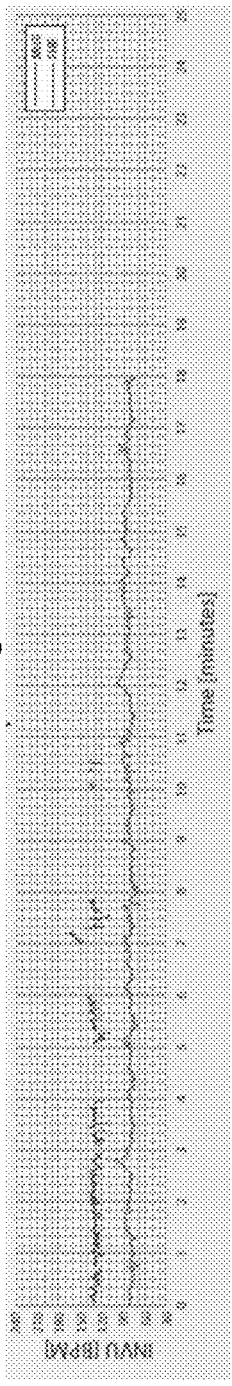
FIG. 9B shows output of an exemplary clinical decision support system for a second patient.

During the course of the study, nine expectant mothers performed a total of thirty (30) remote NSTs. Of the 30 remote NSTs, 27 (i.e., 90%) were deemed as interpretable by the reviewing clinicians. FIG. 9A shows an NST that was deemed as interpretable. FIG. 9B shows an NST that was deemed as uninterpretable.

Figure 9C:
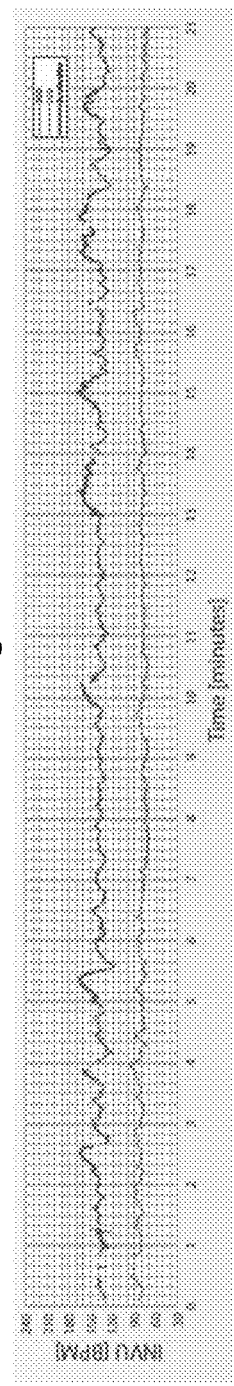
FIG. 9C shows output of an exemplary clinical decision support system for the first patient, having clinical phenomena annotated thereon.

Of the sessions deemed as interpretable, 27 (i.e., 100%) were defined as reactive by the reviewing clinicians. Of these sessions, 25 of 27 (i.e., 92.6%) were also deemed as reactive by the CDSS. FIG. 9C shows the NST of FIG. 9A with the results of the CDSS overlaid showing accelerations identified by the CDSS in a contrasting color. Of the two sessions that were deemed non-reactive by the CDSS, both were borderline cases in terms of ACOG guidelines.

Of the cases deemed reactive by CDSS, the average time to reach reactivity by the CDSS was 22.40±6.68 min. The average length of the NST sessions performed as part of the study was significantly longer: 36.26±16.57 min (t-test, p-value<0.0001). As such, the study demonstrated the feasibility of remote NSTs administered using the CDSS as described herein. Additionally, the study demonstrated that the CDSS as described herein accurately identifies reactivity, which may reduce the length of NST sessions and improve clinician workflow. A poster summarizing the results of the study is attached hereto as Appendix A.

While a number of embodiments of the present invention have been described, it is understood that these embodiments are illustrative only, and not restrictive, and that many modifications may become apparent to those of ordinary skill in the art. For example, all dimensions discussed herein are provided as examples only, and are intended to be illustrative and not restrictive.

What is claimed is:

1. A computer-implemented method, comprising:
   receiving, by a computing device comprising a communication circuitry, a raw bio-potential data set from a plurality of bio-potential sensors disposed within a garment worn by an expectant mother during a fetal heart rate (FHR) session,
      wherein the garment is configured to position and contact the plurality of bio-potential sensors on skin of an abdomen of the expectant mother, and
      wherein the plurality of bio-potential sensors are configured to detect cardiac electrical activity and to output the raw bio-potential data,
   calculating, by the computing device, fetal heart rate data based at least on the raw bio-potential data set,
   generating, by the computing device, data set for the expectant mother during a time window,
      wherein the input data set comprises at least the fetal heart rate data;
   completing, by the computing device, the input data set with at least one missing data sample to provide a completed data set;
   removing, by the computing device, at least one segment from the completed data set based on at least one criterion to provide a corrected data set;
   calculating, by the computing device, a baseline fetal heart rate based at least on the corrected data set;
   detecting, by the computing device, at least one event occurring during the time window based at least on at least one of the corrected data set or the baseline fetal heart rate;
   classifying, by the computing device, the at least one event as either an acceleration, a deceleration, or a baseline change based at least on at least one of the corrected data set or the baseline fetal heart rate; and
   classifying, by the computing device, the FHR session as reactive based on a determination that at least two accelerations were detected during the FHR session; and
   generating, by the computing device, an FHR session output indicative of the classification of the FHR session as reactive; and
   transmitting, by the computing device, via the communication circuitry, an instruction to display on a graphical interface associated with the user, the FHR session output to enable at least one action being taken with respect to the expectant mother.

2. The method of claim 1, wherein the at least one criterion for the step of removing the at least one segment from the completed data set comprises removing the at least one segment based on the at least one segment including a periodic change in the fetal heart rate.

3. The method of claim 2, wherein the periodic change in the fetal heart rate includes at least one of (a) the fetal heart rate varying by more than 25 beats per minute in consecutive samples or (b) applying a threshold based on median and standard deviation.

4. The method of claim 1, further comprising:
   determining, by the computing device, whether the input data set is valid or is not valid; and
   if the input data set is determined to be not valid, receiving a further input data set prior to the step of performing the completing, by the computing device, the input data set, wherein the step of completing, by the computing device, the input data set is performed on the further input data set.

5. The method of claim 4, wherein the step of determining whether the input data set is valid or is not valid is performed by a process comprising:
   identifying, by the computing device, plurality of stable segments of the corrected data set,
      wherein each stable segment comprises a sequence of a predetermined quantity of consecutive samples having a fetal heart rate variability that is less than a predetermined threshold variability;
   determining, by the computing device, a total duration of the plurality of stable segments; and
   determining, by the computing device, whether the input data set is valid or is not valid based at least on a comparison of the total duration of the plurality of stable segments to a predetermined threshold duration.

6. The method of claim 1, wherein the step of determining, by the computing device, the baseline fetal heart rate is performed by a process comprising:
   calculating, by the computing device, a virtual baseline fetal heart rate;

calculating, by the computing device, a virtual high fetal heart rate limit;

calculating, by the computing device, a virtual low fetal heart rate limit;

removing, by the computing device, outlier data points from the corrected data set, wherein outlier data points are data points having a fetal heart rate higher than the virtual high fetal heart rate limit or having a fetal heart rate lower than the virtual low fetal heart rate limit; and calculating, by the computing device, the baseline fetal heart rate based at least on applying rounding to the corrected data set following removing the outlier data points.

7. The method of claim 6, wherein the virtual baseline fetal heart rate is a mean average of fetal heart rates in the corrected data set.

8. The method of claim 6, wherein the steps of calculating the virtual high fetal heart rate limit and calculating the virtual low fetal heart rate limit are performed by a process comprising:

calculating, by the computing device, a standard deviation for the virtual baseline fetal heart rate;

calculating, by the computing device, the virtual high fetal heart rate limit as the virtual baseline fetal heart rate plus two times the standard deviation; and calculating, by the computing device, the virtual low fetal heart rate limit as the virtual baseline fetal heart rate minus two times the standard deviation.

9. The method of claim 1, wherein at least one of the at least one event is classified as an acceleration, and wherein the at least one of the at least one event is classified as an acceleration based on a process comprising:

identifying, by the computing device, a first intersection between a trace of the corrected data set and the baseline fetal heart rate;

identifying, by the computing device, a second intersection between the trace of the corrected data set and the baseline fetal heart rate;

identifying, by the computing device, a maximum fetal heart rate during a time interval between the first intersection and the second intersection; and identifying, by the computing device, the time interval as including the acceleration based at least on a duration of the time interval and the maximum fetal heart rate during the time interval.

10. The method of claim 9, wherein the step of identifying the time interval as including the acceleration is further based on a gestational week of the expectant mother.

11. The method of claim 9, further comprising:

determining, by the computing device, fetal heart rate baseline variability.

12. The method of claim 11, wherein the step of determining, by the computing device, the fetal heart rate baseline variability is performed by a process comprising:

determining, by the computing device, a highest fetal heart rate during a variability time interval following the second intersection, wherein the variability time interval extends from the second intersection until a sooner of (1) a predetermined duration following the second intersection or (2) onset of a subsequent acceleration or deceleration;

determining, by the computing device, a lowest fetal heart rate during the variability time interval; and subtracting, by the computing device, the lowest fetal heart rate during the variability time interval from the highest fetal heart rate during the variability time interval to provide the fetal heart rate baseline variability.

13. The method of claim 1, wherein the at least one event comprises a deceleration, and wherein the at least one event is classified as a deceleration based on a process comprising:

identifying, by the computing device, a first intersection between a trace of the corrected data set and the baseline fetal heart rate;

identifying, by the computing device, a second intersection between the trace of the corrected data set and the baseline fetal heart rate;

identifying, by the computing device, a minimum fetal heart rate during a time interval between the first intersection and the second intersection; and identifying, by the computing device, the time interval as including the deceleration based at least on a difference between the baseline fetal heart rate and the minimum fetal heart rate during the time interval.

14. The method of claim 13, further comprising:

classifying, by the computing device, the deceleration as one of an early deceleration, a late deceleration, a variable deceleration, or a prolonged deceleration.

15. The method of claim 14, wherein the input data set further comprises a uterine contraction signal, and wherein the deceleration is classified as the one of the early deceleration, the late deceleration, the variable deceleration, or the prolonged deceleration based on a process comprising:

determining, by the computing device, a delay, wherein the delay is an amount of elapsed time between the first intersection and a time of the minimum fetal heart rate during the time interval;

determining, by the computing device, a time of a peak of a uterine contraction during the time interval;

determining, by the computing device, a time difference between the time of the minimum fetal heart rate during the time interval and the time of the peak of the uterine contraction signal during the time interval; and classifying, by the computing device, the deceleration as the one of the early deceleration, the late deceleration, the variable deceleration, or the prolonged deceleration based at least on the delay, the time difference, and a duration of the uterine contraction.

16. The method of claim 1, wherein two iterations of the steps of (1) removing, by the computing device, at least one segment from the completed data set based on at least one criterion to provide a corrected data set, (2) calculating, by the computing device, a baseline fetal heart rate based at least on the corrected data set, and (3) detecting, by the computing device, at least one event occurring during the time window based at least on at least one of the corrected data set or the baseline fetal heart rate, are performed for the time window.

17. The method of claim 1, further comprising repeating, for a subsequent time window, the steps of:

receiving, by the computing device, data set for the expectant mother;

completing, by the computing device, the input data set with at least one missing data sample to provide a completed data set;

removing, by the computing device, at least one segment from the completed data set based on at least one criterion to provide a corrected data set;

calculating, by the computing device, a baseline fetal heart rate based at least on the corrected data set;

detecting, by the computing device, at least one event occurring during the time window based at least on at least one of the corrected data set or the baseline fetal heart rate; and classifying, by the computing device, the at least one event as either an acceleration, a deceleration, or a baseline change based at least on at least one of the corrected data set or the baseline fetal heart rate.

18. The method of claim 17, wherein the subsequent time window does not overlap the time window.

19. The method of claim 17, wherein the subsequent time window overlaps the time window by an overlap duration.

20. The method of claim 19, wherein the overlap duration is between 5% of a duration of the time window and 95% of the duration of the time window.

* * * * *